United States Patent [19]

Prosser

[11] Patent Number: 5,285,782
[45] Date of Patent: Feb. 15, 1994

[54] METHOD AND APPARATUS FOR IMPROVING THE ACCURACY OF PULSE TRANSMITTANCE OXIMETER

[75] Inventor: Stephen J. Prosser, Bothell, Wash.

[73] Assignee: Physio-Control Corporation, Redmond, Wash.

[21] Appl. No.: 822,543

[22] Filed: Jan. 17, 1992

[51] Int. Cl.⁵ .................................................. A61B 5/00
[52] U.S. Cl. ..................................... 128/633; 128/664; 128/666; 128/667; 356/41
[58] Field of Search ................ 128/633, 634, 664, 665, 128/666–667; 356/39, 41

[56] References Cited

U.S. PATENT DOCUMENTS

| | | | |
|---|---|---|---|
| 4,714,341 | 12/1987 | Hamaguri et al. | 356/41 |
| 4,960,126 | 10/1990 | Conlon et al. | 128/633 |
| 5,078,136 | 1/1992 | Stone et al. | 128/633 |
| 5,111,817 | 5/1992 | Clark et al. | 128/633 |
| 5,137,023 | 8/1992 | Mendelson et al. | 128/633 |

*Primary Examiner*—Angela D. Sykes
*Attorney, Agent, or Firm*—Christensen, O'Connor, Johnson & Kindness

[57] ABSTRACT

A method and apparatus for accurately determining a blood parameter that is calculated by measuring the transmittance of light through tissue having blood flowing therein is disclosed. A plurality of transmittance of light measurements are obtained for each transmittance of light parameter. The arithmetic mean of each transmittance of light parameter is calculated from the plurality of measurements. The arithmetic means are used to calculate the blood parameter from known formulations.

4 Claims, 1 Drawing Sheet

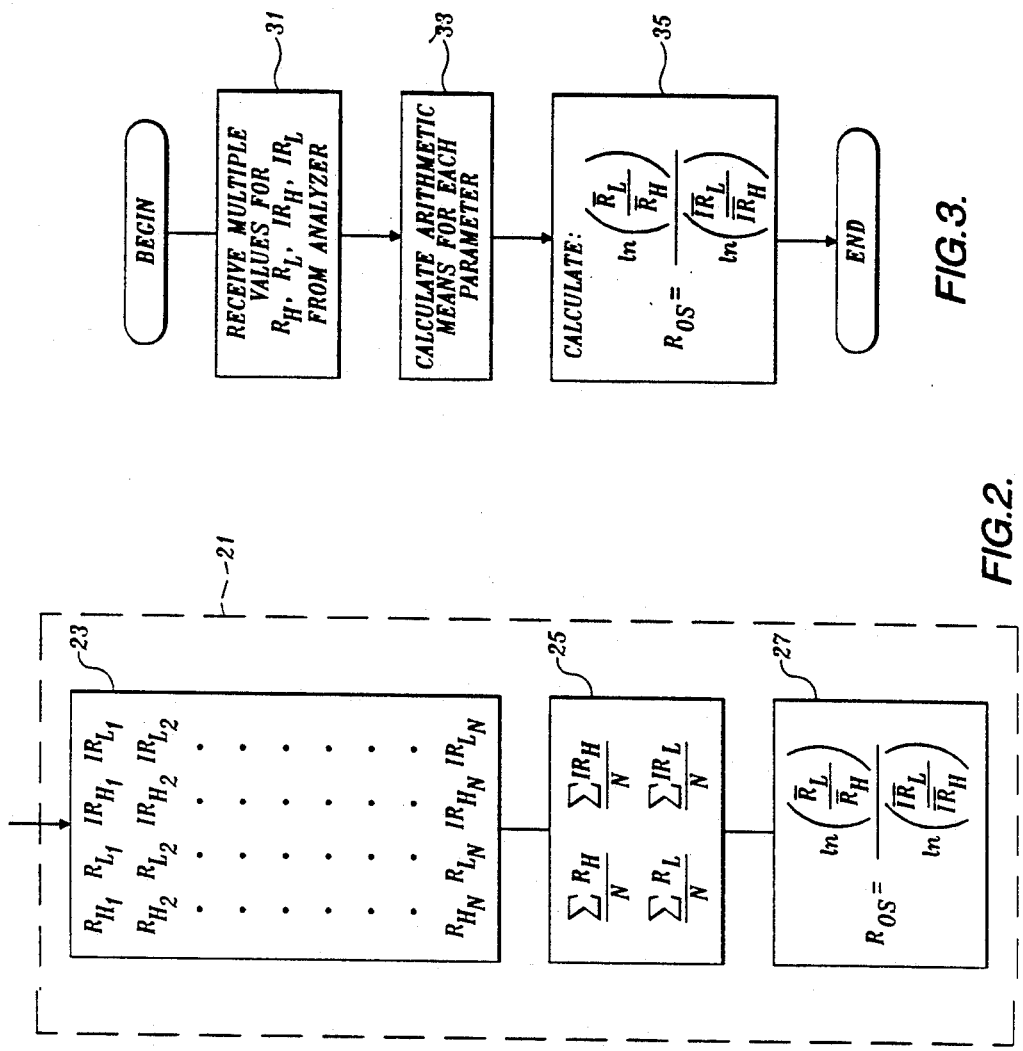
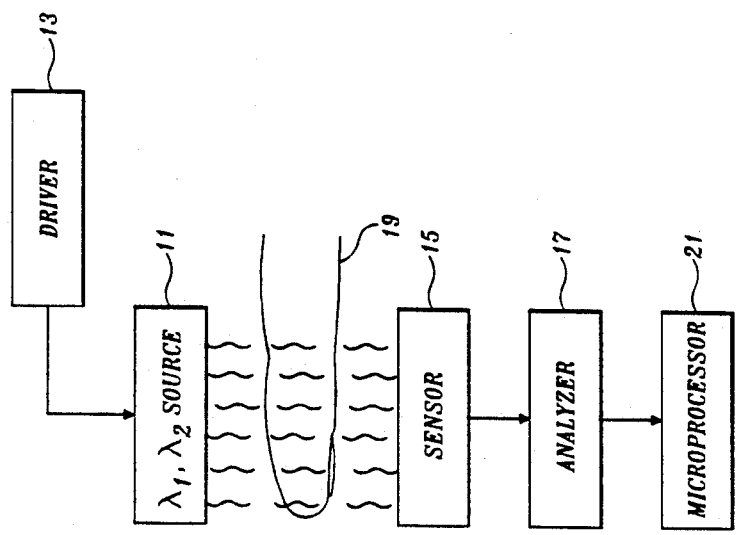

METHOD AND APPARATUS FOR IMPROVING THE ACCURACY OF PULSE TRANSMITTANCE OXIMETER

FIELD OF THE INVENTION

The invention relates to measuring a blood parameter by measuring the transmissivity of light through tissue having blood flowing therein and, more particularly, to an improved method for determining said blood parameter.

BACKGROUND OF THE INVENTION

It is known that various blood parameters may be calculated by measuring the transmittance of light at different wavelengths through tissue having blood flowing therein. Examples of such blood parameters include carbon monoxide, carbon dioxide, glucose, and oxygen concentrations. Accurate information on these blood parameters may be important for a variety of reasons. For example, in the operating room, up-to-date information regarding oxygen saturation can be used to signal changing physiological factors, the malfunction of anaesthesia equipment, or physician error. Similarly, in the intensive care unit, oxygen saturation information can be used to confirm the provision of proper patient ventilation and allow the patient to be withdrawn from a ventilator at an optimal rate.

The non-invasive technique of measuring the transmittance of light in order to formulate blood parameter information is desirable in many applications for reasons of operator convenience and patient comfort. One well-known technique is pulse transmittance oximetry. This technique generally involves measuring the transmittance of light through body tissue at two different wavelengths. Typically, the two wavelengths are in the red and infrared regions. The measurements are made at both systolic pressure and diastolic pressure. In one known formulation, the arterial oxygen saturation ratio in given by the formula:

$$R_{OS} = \frac{\ln \frac{R_L}{R_H}}{\ln \frac{IR_L}{IR_H}}$$

where $R_{OS}$ is the oxygen saturation ratio, $R_L$ is the transmittance of light at the red wavelength through the body tissue at systolic pressure, $R_H$ is the transmittance of light at the red wavelength through the body tissue at diastolic pressure, $IR_L$ is the transmittance of light at the infrared wavelength through the body tissue at systolic pressure, and $IR_H$ is the transmittance of light at the infrared wavelength through the body tissue at diastolic pressure. The actual value of oxygen saturation may be ascertained from the $R_{OS}$ value using empirically derived calibration curves. The precise description of the method and apparatus for measuring the transmittance of light is not part of the present invention and so is described only generally. Reference to U.S. Pat. No. 4,819,646 entitled "Feedback-Controlled Method and Apparatus for Processing Signals Used in Oximetry" to Cheung et al. is recommended for a detailed description of pulse transmittance oximetry.

Moreover, although only a formulation for the oxygen saturation ratio is given above, formulations for carbon dioxide, carbon monoxide, and other blood parameters based upon measurements of the transmittance of light are known in the art. The present invention is equally applicable to those formulations and although the following description of the preferred embodiment relates to pulse transmittance oximetry, it should not be construed to be limiting the scope of the present invention.

As seen in the equation for $R_{OS}$, four parameters must be measured: $R_L$, $R_H$, $IR_L$, and $IR_H$. In any measurement technique where a physical parameter must be measured, random noise errors may arise. Noise errors in measured parameters contribute to inaccuracies in the calculated values based upon the measured parameters; in this case, error in the oxygen saturation ratio $R_{OS}$. In order to more accurately calculate oxygen saturation ratios, various methods have been utilized in the prior art.

One well known and easy to implement method is averaging. In this method, multiple calculated values of $R_{OS}$ are averaged to provide a "smoothed" final value. Because the value of $R_{OS}$ is obtained as a quotient of measured parameters, it has been found that post calculation averaging does not provide optimum noise elimination. An improvement is to average only certain values of $R_{OS}$. In particular, "outliers" are eliminated from the values of $R_{OS}$ before the average is taken. Outliers are values for $R_{OS}$ that are outside a predetermined range from the past history of $R_{OS}$ values. Again, it has been found that even with this improvement, optimum noise elimination is not obtained.

The present invention is directed towards providing an improved method of eliminating random noise error.

SUMMARY OF THE INVENTION

A method and apparatus for reducing random error in a blood parameter calculation is disclosed. The transmittance of light through tissue having blood flowing therein is measured at a plurality of wavelengths at both systolic pressure and diastolic pressure. For each measured transmittance of light parameter, a plurality of measurements are made and the arithmetic average of each measurement parameter is determined. The arithmetic averages of each transmittance of light parameter are utilized to calculate a value for the blood parameter in accordance with known formulations.

In accordance with other aspects of the present invention, the blood parameter to be calculated is an oxygen saturation ratio that is given by:

$$R_{OS} = \frac{\ln \frac{\overline{R_L}}{\overline{R_H}}}{\ln \frac{\overline{IR_L}}{\overline{IR_H}}}$$

where $R_{OS}$ is the oxygen saturation ratio, $\overline{R_L}$ is the arithmetic average of the transmittance of light at the red wavelength through the body tissue at systolic pressure, $\overline{R_H}$ is the arithmetic average of the transmittance of light at the red wavelength through the body tissue at diastolic pressure, $\overline{IR_L}$ is the arithmetic average of the transmittance of light at the infrared wavelength through the body tissue at systolic pressure, and $\overline{IR_H}$ is the arithmetic average of the transmittance of light at the infrared wavelength through the body tissue at diastolic pressure.

It has been found that averaging the values of the parameter measurements prior to determining the value of $R_{OS}$ is more accurate than averaging the values of $R_{OS}$ based on separate sets of parameter measurements.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a block diagram illustrating a pulse oximeter formed in accordance with the present invention;

FIG. 2 is a detailed block diagram illustrating the present invention; and

FIG. 3 is a flow chart illustrating the method of the present invention.

DETAILED DESCRIPTION OF THE PREFERRED EMBODIMENT

As noted above, the present invention may be utilized to improve the accuracy of blood parameters that are calculated using measurements of the transmittance of light through tissue having blood flowing therein. For the blood parameter of oxygen saturation, the following description describes a preferred embodiment. It can be appreciated that the present invention may be utilized in conjunction with other blood parameter calculations using measurements of the transmittance of light.

The calculation of the level of oxygen saturation in blood by pulse transmittance oximetry involves the calculation of an oxygen saturation ratio, $R_{OS}$. From the oxygen saturation ratio, the blood oxygen saturation level may be derived from empirically derived calibration curves. In one known technique, $R_{OS}$ is given by Equation (1) below:

$$R_{OS} = \frac{\ln \frac{R_L}{R_H}}{\ln \frac{IR_L}{IR_H}} \quad (1)$$

where $R_{OS}$ is the oxygen saturation ratio, $R_L$ is the transmittance of light at a red wavelength through the body tissue at systolic pressure, $R_H$ is the transmittance of light at the red wavelength through the body tissue at diastolic pressure, $IR_L$ is the transmittance of light at an infrared wavelength through the body tissue at systolic pressure, and $IR_H$ is the transmittance of light at the infrared wavelength through the body tissue at diastolic pressure. A detailed description of pulse transmittance oximetry and oxygen saturation ratio calculations is contained in U.S. Pat. No. 4,819,646 to Cheung et al. and incorporated herein by reference.

As seen above, $R_{OS}$ is calculated from four measured parameters: $R_L$, $R_H$, $IR_L$, and $IR_H$. Each of these measured parameters contain errors due to random noise. The noise errors in each parameter may affect the calculated $R_{OS}$ value differently, depending upon how the parameter is utilized in Equation (1). For example, noise in the $R_L$ parameter will not have the same effect on the oxygen saturation ratio as noise in the $R_H$ parameter. One common technique of eliminating noise errors in measured parameters is the use of data smoothing techniques such as averaging. However, simple post calculation averaging of multiple calculated values of $R_{OS}$ does not provide for optimal noise reduction. As described below, the present invention reduces random noise errors by averaging the measured parameters prior to calculation of the oxygen saturation ratio.

Referring to FIG. 1, a conventional pulse transmittance oximeter includes a light source 11, a driver 13, a sensor 15, an analyzer 17, and microprocessor 21. The light source 11 generates light at two different wavelengths —a red wavelength, $\lambda_1$, and an infrared wavelength, $\lambda_2$. The light source 11 is powered and controlled by driver 13. During operation, human tissue with blood flowing therein, such as a finger 19, is disposed between light source 11 and the sensor 15, typically a photodiode. Light source 11 is alternately switched to emit either light of the red wavelength or light of the infrared wavelength. Light passing through finger 19 is received by sensor 15. The sensor signals are supplied to analyzer 17. The magnitude of the light received by the sensor 15 at each of the wavelengths $\lambda_1$ and $\lambda_2$ is related to the light transmittance of finger 19. Sensor measurements are made by the analyzer 17 at both wavelengths at both systolic and diastolic pressure.

Thus, the analyzer 17 measures a set of four values, one for each of the parameters $R_L$, $R_H$, $IR_L$, and $IR_H$. Optimally, one set of measured values for the parameters may be measured for each heartbeat. Therefore, seventy-two sets of measured values for the parameters $R_L$, $R_H$, $IR_L$, and $IR_H$ may be measured in one minute for a typical person having a pulse rate of seventy-two beats per minute. Regardless of the rate of measurement over time, a plurality of sets of measured values are supplied to microprocessor 21 by the analyzer 17. The microprocessor 21 calculates the oxygen saturation ratio in accordance with the method of the present invention, which is described next.

Referring to FIG. 2, microprocessor 21 includes an accumulator 23, an averager 25, and a calculator 27. The operation of the microprocessor 21 is shown in FIG. 3. As shown in a block 31, accumulator 23 receives and stores a plurality of sets of measured values for the parameters $R_L$, $R_H$, $IR_L$, and $IR_H$ generated by the analyzer 17. While the exact number of stored sets of measured values is not crucial, the greater the number, the greater the accuracy of the result.

The accumulator 23 supplies the stored sets of measured values to averager 25 that, which as shown in a block 33, computes the arithmetic mean of each of the parameters $R_L$, $R_H$, $IR_L$, and $IR_H$. The set of mean values are supplied to the calculator 27. Using the set of mean values, as shown in a block 35, calculator 27 determines the oxygen saturation ratio using Equation (1). More specifically, the oxygen saturation ratio is given by:

$$R_{OS} = \frac{\ln \frac{\overline{R_L}}{\overline{R_H}}}{\ln \frac{\overline{IR_L}}{\overline{IR_H}}} \quad (2)$$

where $\overline{R_L}$, $\overline{R_H}$, $\overline{IR_L}$ and $\overline{IR_H}$ arithmetic means of $R_L$, $R_H$, $IR_L$, and $IR_H$, respectively, as calculated by averager 25.

In the preferred embodiment described above, one set of mean values is obtained as the arithmetic average of a plurality of sets of measured values. This results in reducing the frequency at which a calculated value of $R_{OS}$ may be obtained. For example, assume that: (1) one set of measured values is obtained every second, (2) one set of mean values is calculated from X sets of measured values, and (3) one calculated value of $R_{OS}$ is obtained from each set of mean values. Therefore, one calculated value of $R_{OS}$ may be obtained every X seconds. In contrast, if the method of the present invention were not employed, then one calculated value of $R_{OS}$ may be obtained from every set of measured values, and thus, every second.

To prevent this reduction in frequency of obtaining $R_{OS}$, in an alternative embodiment, a moving average may be taken such that calculated values of $R_{OS}$ may be calculated at the same rate as the sets of measured values are obtained. Specifically, if we return to the example above of obtaining one set of measured values every second, the sets obtained during the first through fifth seconds may be averaged to give a first set of mean values. The first set of mean values may then be used to calculate $R_{OS}$. Next, the sets obtained during the second through sixth seconds may be averaged to give a second set of mean values. The second set of mean values may then be used to calculated $R_{OS}$. Similarly, the sets obtained during the third through seventh seconds may be averaged to give a third set of mean values. The third set of mean values may then be used to calculated $R_{OS}$. In a like manner, such a moving average may be used to provide one calculated value of $R_{OS}$ every second.

It has been found that averaging each of the parameters $R_L$, $R_H$, $IR_L$, and $IR_H$ prior to calculation of $R_{OS}$ provides a more accurate oxygen saturation value. To appreciate this result, it is first noted that Equation (1) is non-linear in nature. Rather, Equation (1), because it includes ratios, is hyperbolic in nature. In particular, Equation (1) includes the ratios: $R_H/R_L$ and $IR_H/IR_L$. To see how the hyperbolic nature of Equation (1) renders the post calculation averaging solution of the prior art inadequate, a more accurate representation of the measured values of $R_L$, $R_H$, $IR_L$, and $IR_H$ that incorporates noise is needed. Specifically, $$R_L = R_{La} + e(x)_1$$

$$R_H = R_{Ha} + e(x)_2$$

$$IR_L = IR_{La} + e(x)_3$$

$$IR_H = IR_{Ha} + e(x)_4$$

where $R_{La}$, $R_{Ha}$, $IR_{La}$, and $IR_{Ha}$ are the "true and actual values" of the parameters without noise and $e(x)$ represents the error in the measured parameter. Typically, $e(x)$ is variable with each different measurement of $R_L$, $R_H$, $IR_L$, and $IR_H$. Because of the differing errors between measurements, each of the measured parameters $R_L$, $R_H$, $IR_L$, and $IR_H$ will surround the true and actual value. The pattern in which multiple measurements disperse about the true and actual value is referred to as a probability density function (PDF).

As an example illustrating the above, (1) if one hundred measurements of $R_L$ are made, and (2) the true and actual value of $R_L$ is fifty, then the one hundred measured values of $R_L$ will surround the value fifty. Because the error $e(x)$ is evenly distributed with a mean of zero, the average of the one hundred measured values will be fifty. Further, the parameter $R_L$ is said to have an evenly distributed PDF about fifty.

However, although generally all of the measured parameters have evenly distributed PDFs, because of the hyperbolic nature of Equation (1), the PDF of $R_{OS}$ will not be evenly distributed about the true and actual value. The hyperbolic nature of Equation (1) tends to skew the PDF of $R_{OS}$ such that the mean value of $R_{OS}$ is not equal to the true and accurate value. Therefore, post calculation averaging of the oxygen saturation ratio will not produce the true and actual value for the oxygen saturation ratio. In contrast, by pre-averaging each measured parameter, so as to provide the true and actual value of each measured parameter prior to insertion into Equation (1), it has been found that the hyperbolic nature of Equation (1) will not affect the calculated value of $R_{OS}$.

While the preferred embodiment of the invention has been illustrated and described, it will be appreciated that various changes can be made therein without departing from the spirit and scope of the invention. For example, although the pre-averaging method of the present invention has been applied specifically to pulse transmittance oximetry, pre-averaging is effective where a calculated quantity is based upon the ratio of two empirically measured parameters. Moreover, although the present invention is shown applied to one specific equation for determining an oxygen saturation ratio, it can be appreciated that the technique may be applied to any non-linear equations for determining an oxygen saturation ratio. Examples of a different non-linear formulation is the Taylor series approximation of Equation (1). Further, although the present invention has been described in conjunction with a formulation for the oxygen saturation ratio, the present invention is equally applicable to formulations for carbon dioxide, carbon monoxide, and other blood parameters based upon measurement of transmittance of light through tissue having blood flowing therein. Thus, the present invention may be practiced other than as specifically disclosed herein.

The embodiments of the invention in which an exclusive property or privilege is claimed are defined as follows:

1. A method of determining an oxygen saturation ratio of a patient comprising the steps of:
   (a) transmitting light through tissue having arterial blood flowing therein;
   (b) measuring a plurality of light parameters at a predetermined blood flow condition, said predetermined blood flow condition being blood flow at systolic pressure and at diastolic pressure and further wherein said plurality of light parameters is the transmittance of light through said tissue at systolic and diastolic blood pressure wherein said plurality of light parameters includes:
      (i) the transmittance of light of a first wavelength light at systolic pressure and denoted by $R_L$;
      (ii) the transmittance of light of said first wavelength light at diastolic pressure and denoted by $R_H$;
      (iii) the transmittance of light of a second wavelength light at systolic pressure and denoted by $IR_L$; and
      (iv) the transmittance of light of said second wavelength light at diastolic pressure and denoted by $IR_H$;
   (c) obtaining a plurality of values for all of said plurality of light parameters;
   (d) for all of said plurality of light parameters, calculating the arithmetic means of said plurality of values; and (e) after calculating said arithmetic means, determining said blood parameter from said arithmetic means calculated in step (d) in accordance with:

$$R_{OS} = \frac{\ln \frac{\overline{R}_L}{\overline{R}_H}}{\ln \frac{\overline{IR}_L}{\overline{IR}_H}}$$

where $R_{OS}$ is said oxygen saturation ratio, $\overline{R}_L$, $\overline{R}_H$, $\overline{IR}_L$, and $\overline{IR}_H$ are said arithmetic means of step (c).

2. An apparatus for determining an oxygen saturation ratio of a patient comprising:
(a) means for transmitting light through tissue having arterial blood flowing therein;
(b) sensing means for measuring a plurality of light parameters at a predetermined blood flow condition, said predetermined blood flow condition being blood flow at systolic pressure and at diastolic pressure and further wherein said plurality of light parameters is the transmittance of light through said tissue at systolic and diastolic blood pressure wherein said plurality of light parameters includes:
  (i) the transmittance of light of a first wavelength light at systolic pressure and denoted by $R_L$;
  (ii) the transmittance of light of said first wavelength light at diastolic pressure and denoted by $R_H$;
  (iii) the transmittance of light of a second wavelength light at systolic pressure and denoted by $IR_L$; and
  (iv) the transmittance of light of said second wavelength light at diastolic pressure and denoted by $IR_H$;
(c) means for obtaining a plurality of values for at least one of said plurality of light parameters;
(d) averaging means for calculating the arithmetic mean of said plurality of values of said plurality of light parameters; and
(e) calculator means for determining said blood parameter from and after calculation of said arithmetic mean calculated in step (d) in accordance with:

$$R_{OS} = \frac{\ln \frac{\overline{R}_L}{\overline{R}_H}}{\ln \frac{\overline{IR}_L}{\overline{IR}_H}}$$

where $R_{OS}$ is said oxygen saturation ratio, $\overline{R}_L$, $\overline{R}_H$, $\overline{IR}_L$, and $\overline{IR}_H$ are said arithmetic means of step (c).

3. A method for measuring an oxygen saturation ratio comprising the steps of:
(a) transmitting through tissue having arterial blood flowing therein light of a first wavelength and light of a second wavelength;
(b) measuring the transmittance of light at said first wavelength and the transmittance of light at said second wavelength through the tissue at systolic pressure and diastolic pressure, wherein the transmittance of light at said first wavelength at systolic pressure is denoted by $R_L$, the transmittance of light at said first wavelength at diastolic pressure is denoted by $R_H$, the transmittance of light at said second wavelength at systolic pressure is denoted by $IR_L$, and the transmittance of light at said second wavelength at diastolic pressure is denoted by $IR_H$;
(c) obtaining a plurality of measurements for said $R_L$, $R_H$, $IR_L$, and $IR_H$;
(d) calculating the arithmetic mean for said $R_L$, $R_H$, $IR_L$, and $IR_H$ using said plurality of measurements from step (c), said arithmetic means denoted by $\overline{R}_L$, $\overline{R}_H$, $\overline{IR}_L$, and $\overline{IR}_H$ respectively; and
(e) calculating said oxygen saturation ratio in accordance with:

$$R_{OS} = \frac{\ln \frac{\overline{R}_L}{\overline{R}_H}}{\ln \frac{\overline{IR}_L}{\overline{IR}_H}}.$$

4. An apparatus for measuring an oxygen saturation ratio comprising:
(a) a light source for transmitting through tissue having arterial blood flowing therein light of a first wavelength and light of a second wavelength;
(b) detection means for measuring the transmittance of light at said first wavelength and the transmittance of light at said second wavelength at systolic pressure and diastolic pressure, wherein the transmittance of light at said first wavelength at systolic pressure is denoted by $R_L$, the transmittance of light at said first wavelength at diastolic pressure is denoted by $R_H$, the transmittance of light at said second wavelength at systolic pressure is denoted by $IR_L$, and the transmittance of light at said second wavelength at diastolic pressure is denoted by $IR_H$;
(c) means for obtaining a plurality of measurements for said $R_L$, $R_H$, $IR_L$, and $IR_H$;
(d) averaging means for determining the arithmetic mean for said $R_L$, $R_H$, $IR_L$, and $IR_H$ using said plurality of measurements from step (c), said arithmetic means denoted by $\overline{R}_L$, $\overline{R}_H$, $\overline{IR}_L$, and $\overline{IR}_H$ respectively; and
(e) calculating means for calculating said oxygen saturation ratio in accordance with:

$$R_{OS} = \frac{\ln \frac{\overline{R}_L}{\overline{R}_H}}{\ln \frac{\overline{IR}_L}{\overline{IR}_H}}.$$

* * * * *